(12) United States Patent
Gowan

(10) Patent No.: US 10,188,525 B2
(45) Date of Patent: Jan. 29, 2019

(54) SPINAL IMPLANT SYSTEM AND METHOD

(71) Applicant: WARSAW ORTHOPEDIC, INC., Warsaw, IN (US)

(72) Inventor: Carrie L. Gowan, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/094,544

(22) Filed: Apr. 8, 2016

(65) Prior Publication Data
US 2016/0220383 A1 Aug. 4, 2016

Related U.S. Application Data

(62) Division of application No. 14/151,007, filed on Jan. 9, 2014, now Pat. No. 9,364,341.

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/447* (2013.01); *A61F 2/4611* (2013.01); *A61F 2002/30471* (2013.01); *A61F 2002/30517* (2013.01); *A61F 2002/30538* (2013.01); *A61F 2002/30578* (2013.01); *A61F 2002/30774* (2013.01); *A61F 2002/30787* (2013.01); *A61F 2002/4475* (2013.01)

(58) Field of Classification Search
CPC .......................... A61F 2002/4615; A61F 2/447
See application file for complete search history.

(56) References Cited

U.S. PATENT DOCUMENTS

| 6,200,347 | B1 * | 3/2001 | Anderson | A61F 2/28 623/16.11 |
| 7,850,731 | B2 * | 12/2010 | Brittan | A61F 2/4611 623/17.11 |
| 8,328,872 | B2 * | 12/2012 | Duffield | A61F 2/447 623/17.16 |
| 8,343,219 | B2 * | 1/2013 | Allain | A61B 17/0642 606/100 |
| 8,709,054 | B2 * | 4/2014 | Lowry | A61B 17/1671 606/295 |
| 8,709,083 | B2 * | 4/2014 | Duffield | A61F 2/447 623/17.11 |
| 8,852,281 | B2 * | 10/2014 | Phelps | A61F 2/4455 623/17.16 |
| 9,039,774 | B2 * | 5/2015 | Chataigner | A61F 2/442 606/86 A |
| 9,044,337 | B2 * | 6/2015 | Dinville | A61F 2/447 |
| 9,193,627 | B2 | 11/2015 | Dantin et al. | |
| 9,198,775 | B2 * | 12/2015 | Phelps | A61F 2/4455 |

(Continued)

*Primary Examiner* — Jan Christopher Merene

(57) ABSTRACT

A spinal implant comprises an implant body extending between an anterior surface and a posterior surface, and including a first vertebral engaging surface and a second vertebral engaging surface. The implant body further including an inner surface that defines at least a first cavity and a second cavity spaced from the first cavity. The first cavity is oriented to implant a fastener oblique relative to a bilateral axis of a subject body. The second cavity is oriented to implant a fastener in substantial alignment with the bilateral axis. Systems and methods of use are disclosed.

20 Claims, 14 Drawing Sheets

(56) References Cited

U.S. PATENT DOCUMENTS

| | | | |
|---|---|---|---|
| 9,539,105 B2* | 1/2017 | Phelps | A61F 2/4455 |
| 9,615,936 B2* | 4/2017 | Duffield | A61F 2/4455 |
| 10,034,763 B2* | 7/2018 | Phelps | A61F 2/4455 |
| 10,034,765 B2* | 7/2018 | Blain | A61F 2/30771 |
| 2002/0120334 A1* | 8/2002 | Crozet | A61B 17/86 |
| | | | 623/17.11 |
| 2003/0105467 A1* | 6/2003 | Ralph | A61B 17/025 |
| | | | 606/90 |
| 2005/0101960 A1* | 5/2005 | Fiere | A61B 17/7059 |
| | | | 623/17.11 |
| 2005/0107880 A1* | 5/2005 | Shimp | A61F 2/28 |
| | | | 623/17.11 |
| 2006/0085071 A1* | 4/2006 | Lechmann | A61B 17/86 |
| | | | 623/17.11 |
| 2008/0177307 A1* | 7/2008 | Moskowitz | A61B 17/0642 |
| | | | 606/246 |
| 2012/0083890 A1* | 4/2012 | McGahan | A61F 2/4465 |
| | | | 623/17.16 |
| 2012/0185048 A1* | 7/2012 | Phelps | A61F 2/4455 |
| | | | 623/17.16 |
| 2014/0135930 A1* | 5/2014 | Georges | A61F 2/4455 |
| | | | 623/17.16 |
| 2014/0277497 A1* | 9/2014 | Bennett | A61F 2/4455 |
| | | | 623/17.16 |
| 2014/0277513 A1* | 9/2014 | Fessler | A61B 17/8042 |
| | | | 623/17.16 |
| 2014/0336771 A1* | 11/2014 | Zambiasi | A61F 2/4455 |
| | | | 623/17.16 |
| 2015/0134063 A1* | 5/2015 | Steinmann | A61F 2/30907 |
| | | | 623/17.16 |
| 2015/0173915 A1* | 6/2015 | Laubert | A61F 2/447 |
| | | | 623/17.16 |
| 2015/0196400 A1* | 7/2015 | Dace | A61F 2/4455 |
| | | | 623/17.16 |

* cited by examiner

SPINAL IMPLANT SYSTEM AND METHOD

This application is a divisional application of U.S. patent application Ser. No. 14/151,007, filed Jan. 9, 2014, which is incorporated by reference herein, in its entirety.

TECHNICAL HELD

The present disclosure generally relates to medical devices for the treatment of musculoskeletal disorders, and more particularly to a surgical system and method for treating a spine, which can be employed with one or a plurality of surgical pathways for accessing a surgical site adjacent a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. This disclosure describes an improvement over these prior art technologies.

In one embodiment, a spinal implant is provided that comprises an implant body extending between an anterior surface and a posterior surface, and including a first vertebral engaging surface and a second vertebral engaging surface. The implant body includes an inner surface that defines at least a first cavity and a second cavity spaced from the first cavity. The first cavity being oriented to implant a fastener oblique relative to a bilateral axis of a subject body. The second cavity being oriented to implant a fastener in substantial alignment with the bilateral axis. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

Figure 1:
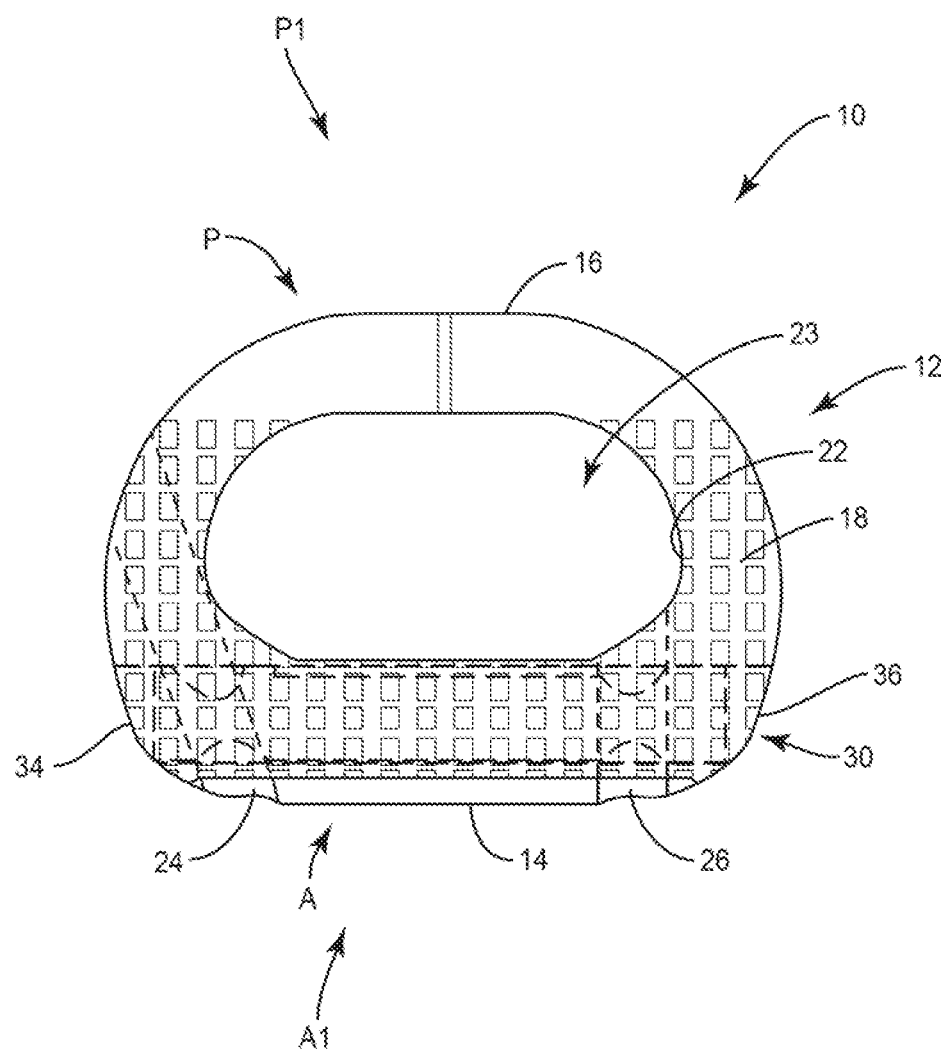
FIG. 1 is a side view, in part phantom, of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine, which can be employed with one or a plurality of surgical pathways. In one embodiment, the systems and methods of the present disclosure are employed with a spinal joint fusion, for example, with a cervical, thoracic, lumbar and/or sacral region of a spine. In one embodiment, an implant is disclosed for performing a spinal joint fusion from an oblique-lateral surgical pathway at a selected oblique angle from the medial plane of a patient or an anterior lateral surgical pathway. In one embodiment, the implant includes an interbody device, a plate and/or bone fasteners. In one embodiment, the implant is employed with an instrument guide configured for use with an oblique-lateral surgical approach. In one embodiment, the implant is employed with an instrument guide configured for use with the anterior lateral surgical approach.

In one embodiment, a surgical system is provided that is employed with a method including an oblique lateral interbody fusion (OLIF) procedure in a lower lumbar region between an L5 vertebral body and a sacrum S1 approach using a location of a retroperitoneal anatomy and related vascular structures, which may include transabdominal and retroperitoneal. In one embodiment, the surgical system is employed with a method including an anterior lateral interbody fusion (ALIF) procedure in the lower lumbar region.

In one embodiment, the surgical system includes a spinal implant that is reversible such that the implant incorporates two different inserter holes in a proximal side of the implant. In one embodiment, the spinal implant can be oriented with a first side towards a cephalad orientation of a subject body such that a perpendicular ALIF inserter hole is accessible to a threaded shaft located on a left side of an ALIF inserter and/or screw guide. The spinal implant can also be rotated or flipped into an or with a second side toward the cephalad orientation such that an oblique OLIF51 inserter hole is disposed, such as, for example, 15 degrees oft direct a anterior axis and/or a bilateral axis of a subject body and is accessible to a threaded shaft located on the left side of an OLIF51 inserter and/or screw guide. This configuration of the spinal implant facilitates converting the spinal implant from an ALIF implant to an OLIF technique and implant. In one embodiment, the spinal implant reduces the amount of inventory and/or cost by providing the same implant body for OLIF51 and ALIF techniques. In one embodiment, the spinal implant facilitates procedures-specific drill guides connected with a plate and/or the implant body.

In one embodiment, the spinal implant includes a modular/reversible combination implant suitable for both ALIF and OLIF procedures by rotating or flipping the implant 180 degrees. In one embodiment, the spinal implant facilitates a 2-in-1 procedure capability in a single implant. In one embodiment, the spinal implant rotates about a pivot point. In one embodiment, the spinal implant includes both ALIF and OLIF inserter holes located on a pivotable rod. In one embodiment, the pivot rod includes a stop for limiting rotation. In one embodiment, the pivot rod is rotatable relative to the implant in a range of rotation of approximately 20 degrees. In one embodiment, the pivot rod is rotatable relative to the implant in a range of rotation of approximately 10 degrees ire one direction and 10 degrees in a second direction.

In one embodiment, the spinal implant is utilized with specialized surgical instruments for each of one or a plurality of surgical approaches. In one embodiment, the implant includes an ALIF plate attached to the reversible implant with an ALIF inserter/guide. In one embodiment, an OLIF plate is attached to the reversible implant with an OLIF inserter/guide. In one embodiment, an ALIF specific modular head drill/tap/screw (DTS) guide is releasably connected with the implant. In one embodiment, an OLIF specific modular head DTS guide is releasably connected with the implant. In one embodiment, the DTS guide attaches to an inserter via a threaded shaft. In one embodiment, the guide is rotatable relative to the spinal implant in a range of rotation of approximately 20 degrees. In one embodiment, the guide is rotatable relative to the spinal implant in a range of rotation of approximately 10 degrees in one direction and 10 degrees in a second direction.

In one embodiment, the DTS guide includes a threaded shaft that is placed through the inserter and the plate, and threaded into a pivot rod of the implant. In one embodiment, a knob of the threaded shaft is rotated clockwise to thread the shaft into the pivot rod such that the inserter comprises a rigid configuration. In some embodiments, this configuration allows the plate to pivot about an interbody device of the implant. In some embodiments, the knob can be rotated, counter-clockwise for example, to back the threaded rod out from the pivot rod to allow movement such that the plate rotates freely around the interbody device.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment, it is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, trilcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of biocompatible polymer, such as PEEK, and selectively mated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Figure 12:
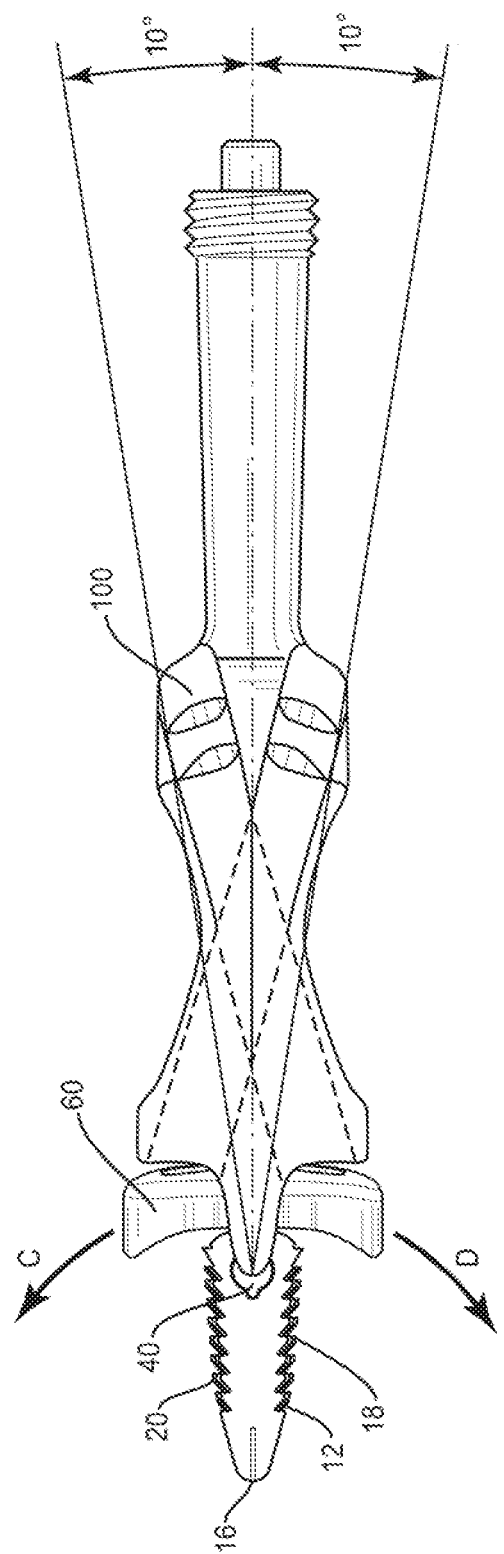
FIG. 12 is a side view of components of one embodiment of a system in accordance with the principles of the present disclosure.
Figure 13:
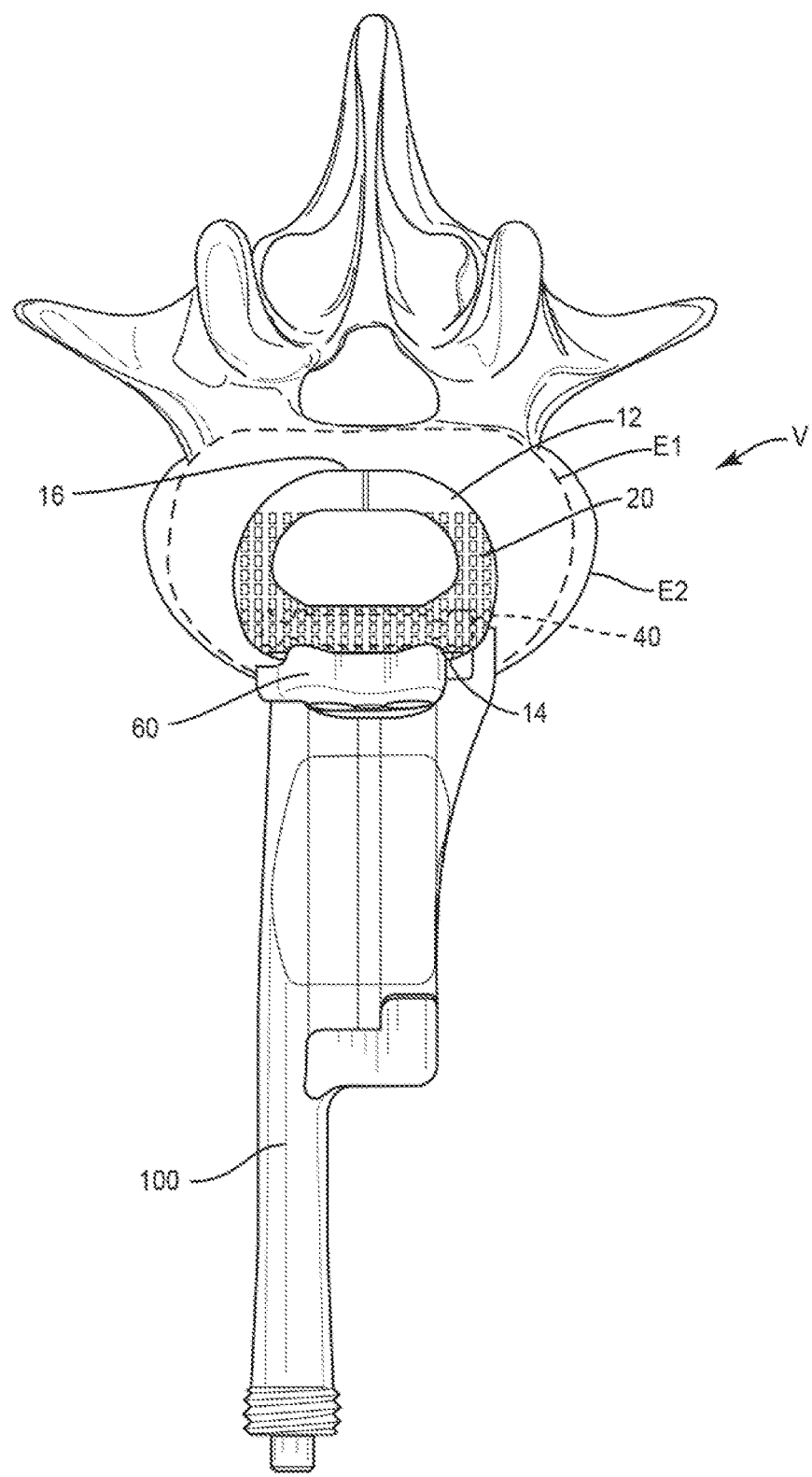
FIG. 13 an axial view of components of one embodiment of a system in accordance with the principles of the present disclosure disposed with vertebrae.

Spinal implant system 10 may be employed, for example, with minimally invasive procedures, including percutaneous techniques, mini-open surgical techniques and/or open surgical techniques to deliver and introduce instrumentation and/or implants, such as, for example, an interbody implant, at a surgical site within a subject body B of a patient, which includes, for example, a spine having vertebrae V, as shown, for example in FIGS. 12 and 13. In some embodiments, the implant can include spinal constructs including one or more bone fasteners, spinal rods, connectors and/or plates. In some embodiments, various components of spinal implant system 10 may be utilized in open or traditional spinal surgical techniques. In some embodiments, a patient is positioned on their side for the surgical procedure and the surgeon may stand on an anterior side of the patient to be capable of standing directly above the oblique-anterior and/or oblique lateral surgical pathway.

Figure 14:
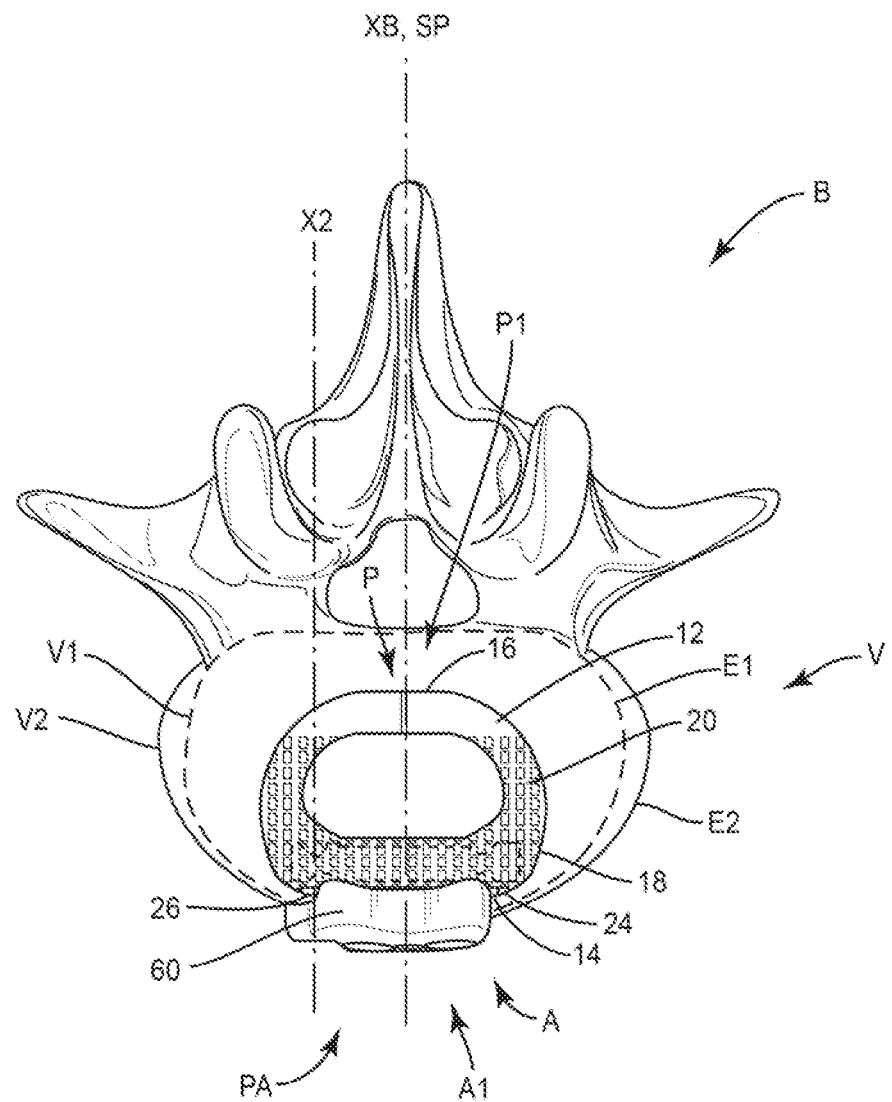
FIG. 14 is an axial view of components of the system and vertebrae shown in FIG. 13.

Spinal implant system 10 includes an interbody implant 12. Interbody implant 12 has an implant body that extends between an anterior surface 14 defining an anterior face A and a posterior surface 16 defining a posterior face P. In some embodiments, upon disposal of interbody implant 12 with vertebrae, anterior face A is oriented to face an anterior side of body B and be disposed adjacent an anterior portion of vertebrae, such as, for example, an anterior portion A1 of an intervertebral space of vertebrae V, as shown in FIG. 14. In some embodiments, at least a portion of anterior face A defines an axis and/or plane substantially aligned with anterior portion A1 and oriented perpendicular to a bilateral axis XB of body B, upon disposal of interbody implant 12 with vertebrae V. In some embodiments, upon disposal of interbody implant 12 with vertebrae V, posterior face P can be disposed at various angular orientations relative to axis XB. In some embodiments, upon disposal of interbody implant 12 with vertebrae, posterior face P is oriented to face a posterior side of body B and be disposed adjacent a posterior portion of vertebrae, such as, for example, a posterior portion P1 of an intervertebral space of vertebrae V. In some embodiments, at least a portion of posterior face P defines an axis and/or plane substantially aligned with posterior portion P1 and oriented perpendicular to bilateral axis XB, upon disposal of interbody implant 12 with vertebrae V. In some embodiments, upon disposal of interbody implant 12 with vertebrae V, posterior face P can be disposed at various angular orientations relative to axis XB.

Interbody implant 12 includes a vertebral engaging surface 18 and a vertebral engaging surface 20. Surface 20 is substantially planar and configured to engage endplate tissue of a vertebral body, such as, for example, an endplate E1, shown in phantom in FIG. 13. Surface 18 is configured to engage endplate tissue of a vertebral body, such as, for example, an endplate E2. In some embodiments, surface 18 and/or surface 20 may be rough, textured, porous, semi-porous, dimpled, knurled, toothed, grooved and/or polished to facilitate engagement with tissue. In some embodiments, the vertebral tissue may include intervertebral tissue, endplate surfaces and or cortical bone.

Interbody implant 12 is a modular reversible implant such that surface 18 or surface 20 is disposable with vertebrae V in a cephalad and/or caudal orientation with body B. For example, upon selection of an OLIF surgical approach and/or a variation thereof, as described for example with regard to FIG. 19, interbody implant 12 is configured such that surface 18 is disposable in a cephalad orientation and surface 20 is disposable in a caudal orientation of a body to facilitate delivery of interbody implant 12 along the OLIF approach and/or pathway and for fixation of interbody implant 12 with vertebrae V, as discussed herein.

Interbody implant 12 may be rotated or flipped for employment of interbody implant 12 with an ALIF surgical approach and/or variations thereof, as described for example with regard to FIG. 14, such that surface 18 is disposable in a caudal orientation and surface 20 is disposable in a cephalad orientation to facilitate delivery of interbody implant 12 along the ALIF approach and/or pathway and for fixation with vertebrae V. In some embodiments, interbody implant 12 may be rotated prior to delivery to a surgical site or subsequent to selection of a first surgical approach such as an OLIF approach and then alternated to a second surgical approach such as an OLIF approach.

Interbody implant 12 includes an inner surface 22 that defines an opening 23 configured to receive an agent, which may include bone graft (not shown) and/or other materials, as described herein, for employment in a fixation or fusion treatment. In some embodiments, the cross-sectional geometry of interbody implant 12 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. Interbody implant 12 includes an outer surface 25 that is smooth or even. In some embodiments, outer surface 25 may be textured, rough, porous, semi-porous, dimpled and/or polished.

Figure 4:
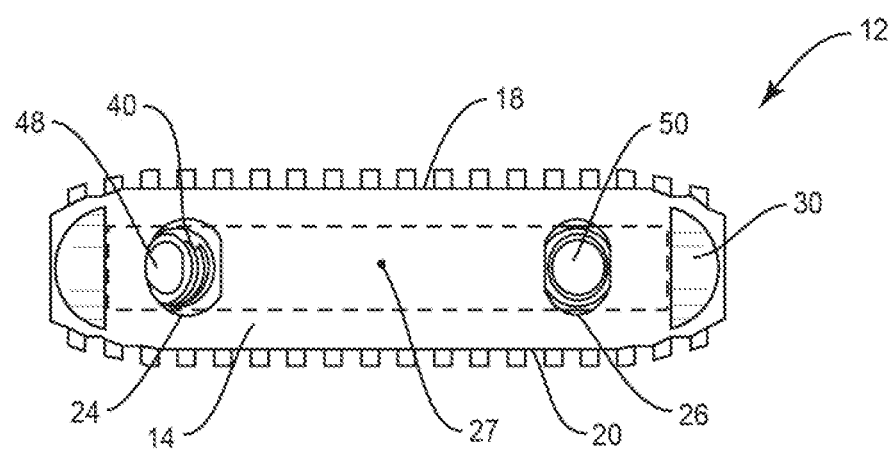
FIG. 4 is a side view of the components shown in FIG. 1.
Figure 19:
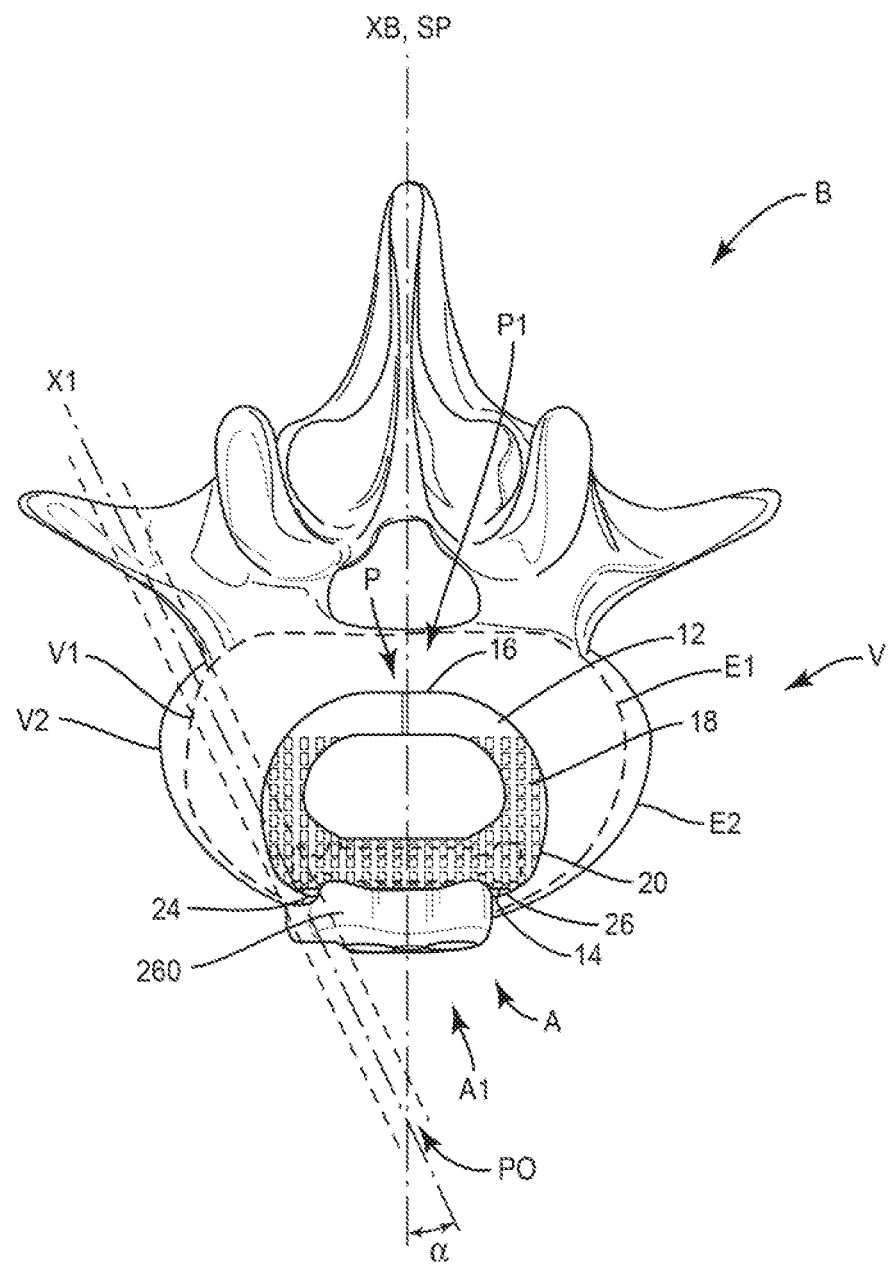
FIG. 19 is an axial view of components of the system and vertebrae shown in FIG. 18.

Surface 22 defines a cavity, such as, for example, a passageway 24, as shown in FIG. 1 in phantom and in FIG. 4, oriented to implant a fastener oblique relative to axis XB and a cavity, such as, for example, a passageway 26 oriented to implant a fastener in substantial parallel alignment with axis XB. All or only a portion of surface 22 that defines passageway 24 defines an internally threaded portion. Passageway 24 extends along the body of interbody implant 12 in a transverse configuration relative to faces A, P. In some embodiments, upon disposal of interbody implant 12 with vertebrae V, passageway 24 is oriented with interbody implant 12 in substantial alignment with an oblique surgical pathway PO, as shown in FIG. 19, formed with body 6, as described herein. For example, passageway 24 is disposed in substantial alignment with surgical pathway PO, which is oriented oblique relative to bilateral axis XB. In some embodiments, substantial alignment of all or only a portion of passageway 24 with all or only a portion of surgical pathway PO includes co-axial, spaced apart, offset and/or angularly offset.

In some embodiments, passageway 24 defines an axis X1 oriented oblique relative to axis XB such that passageway 24 implants a fastener, as described herein, oblique relative to axis XB and adjacent portion A1. Axis XB lies in a sagittal plane SP defined by vertebrae V. Axis X1 is disposed in substantial alignment with surgical pathway PO and at an oblique angle α relative to axis XB. In some embodiments, angle α is in a range of approximately 0-60 degrees. In one embodiment, angle α is approximately 15 degrees relative to ax XB and substantially aligned with surgical pathway PO such that passageway 24 is configured to receive a fastener via surgical pathway PO.

Passageway 26, as shown in FIG. 14, defines an axis X2 oriented parallel relative to axis XB such that passageway 26 implants a fastener, as described herein, parallel relative to axis XB and adjacent portion A1. Passageway 26 extends perpendicular to faces A, P. Passageway 26 is oriented with the body of interbody implant 12 in substantial alignment with an anterior surgical pathway PA formed in body B, as described herein. Surgical pathway PA is oriented parallel relative to axis XB and sagittal plane SP of body B. In some embodiments, as shown in FIG. 4, interbody implant 12 is rotatable about a pivot point 27 to facilitate selected orientation of passageways 24, 26, as described herein.

Figure 2:
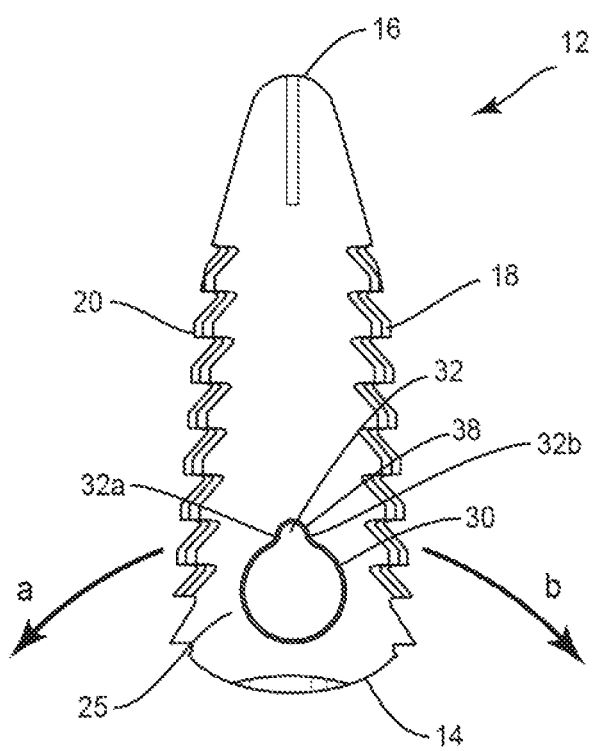
FIG. 2 is a side view of the components shown in FIG. 1.

Surface 22 defines a cavity such as, for example, a transverse bore 30, as shorn in FIGS. 1 and 2, configured for disposal of a member configured to facilitate rotation of a plate and/or a guide, as discussed herein. Bore 30 extends substantially parallel to surface 14 and is defined by an inner surface 32. Bore 30 extends between openings 34, 36 of surface 25. In some embodiments, bore 30 may extend transverse to surface 14. In some embodiments, bore 30 may have various cross-section configurations, such as, for example, round, oval, oblong, triangular, polygonal having planar or arcuate side portions, irregular, uniform, non-uniform, consistent, variable or horseshoe shape.

Surface 32 defines a recess 38 disposed along all or only a portion of bore 30, for example, adjacent openings 34, 36. Recess 38 is engageable with a stop of the member, as described herein, to limit a range of movement of the member between a first movable limit and a second movable limit.

Figure 3:
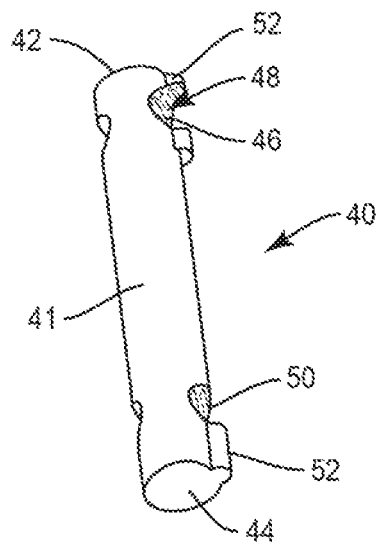
FIG. 3 is a perspective view of one embodiment of a component of the system shown in FIG. 1.

Interbody implant 12 includes a member such as, for example, a pivot rod 40, as shown in FIG. 3, configured for movable disposal within bore 30. Pivot rod 40 has a cylindrical cross-section. In some embodiments, pivot rod 40 may have various cross-section configurations, such as, for example, oval, oblong, triangular, polygonal having planar or arcuate side portions, irregular, uniform, non-uniform, consistent, variable or horseshoe shape. Pivot rod 40 extends through bore 30 and includes an end 42 disposed with opening 34 and an end 44 disposed with opening 36.

Pivot rod 40 includes an inner surface 46 that defines a cavity 48 and a cavity 50. Cavity 48 is disposed adjacent end 42 and forms a portion of passageway 24. All or only a portion of surface 46 that defines cavity 48 defines an internally threaded portion. Cavity 50 is disposed adjacent end 44 and forms a portion of passageway 26. All or only a portion of surface 46 that defines cavity 50 defines an internally threaded portion.

Cavity 46 is pivotable relative to interbody implant 12 for orientation with passageway 24 to implant a fastener oblique relative to axis XB, as described herein. Cavity 50 is pivotable relative to interbody implant 12 for orientation with passageway 26 to implant a fastener in substantial alignment with axis XB. Cavity 48 is disposed in a transverse configuration relative to faces A, P. In some embodiments, upon disposal of interbody implant 12 with vertebrae V, cavity 48 is oriented with interbody implant 12 in substantial alignment with surgical pathway PO, as shown in FIG. 19, as described herein, which is oriented oblique relative to axis XB. Cavity 50, as shown in FIG. 14, extends perpendicular to faces A, P. Cavity 50 is oriented with the body of interbody implant 12 in substantial alignment with surgical pathway PA, as described herein.

Pivot rod 40 is pivotable relative to interbody implant 12 to facilitate alignment of cavities 48, 50 with passageways 24, 26. In some embodiments, pivot rod 40 is rotatable relative to interbody implant 12 via a guide instrument in a range of rotation of approximately 20 degrees, as discussed herein. In one embodiment, pivot rod 40 is rotatable relative to interbody implant 12 in a range of 10 degrees in a first direction and 10 degrees in a second direction. Rotation of pivot rod 40 facilitates positioning of interbody implant 12 with an intervertebral space.

Each of ends 42, 44 include a flange, such as for example, a stop 52 configured to engage opposing limit surfaces 32a, 32b of surface 32 that define recess 38. As such, recess 38 defines a gap or range of movement for pivotal movement of rod 40 relative to interbody implant 12. Limit surfaces 32a, 32b are engageable with stop 52 to limit a range of movement of pivot rod 40 between a first movable limit defined by engagement with surface 32a, in a first direction shown by snow a in FIG. 2, and a second movable limit defined by engagement with surface 32b, in a second direction shown by arrow b. Stop 52 is configured to resist and/or prevent rotation of pivot rod 40 in the first direction and the second direction. Stop 52 is configured to engage limit surfaces 32a, 32b such that rotation of pivot rod 40 is limited to a selective degree of rotation and to allow the practitioner to maintain control over the movement and positioning of interbody implant 12.

Figure 7:
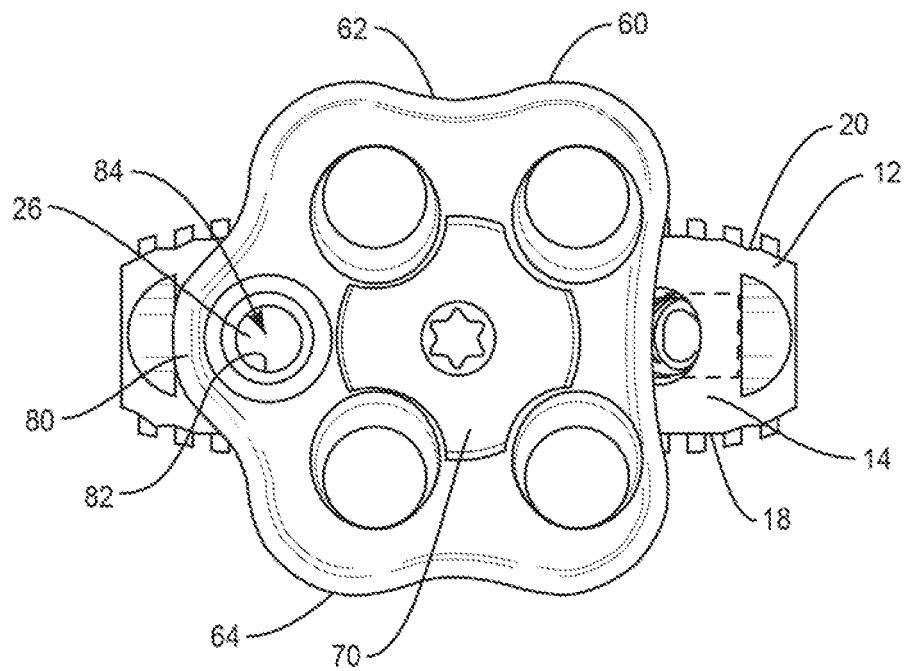
FIG. 7 is a side view of components of one embodiment of a system in accordance with the principles of the present disclosure.
Figure 8:
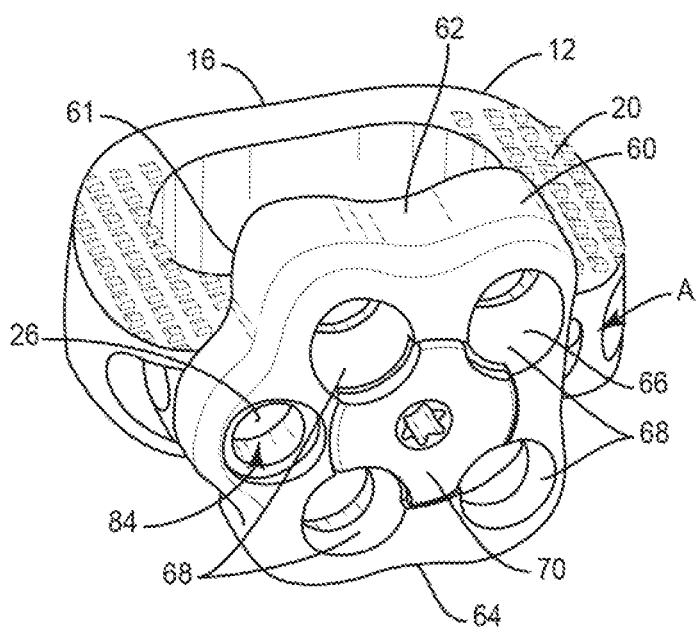
FIG. 8 is a perspective view of the components shown in FIG. 7.
Figure 9:
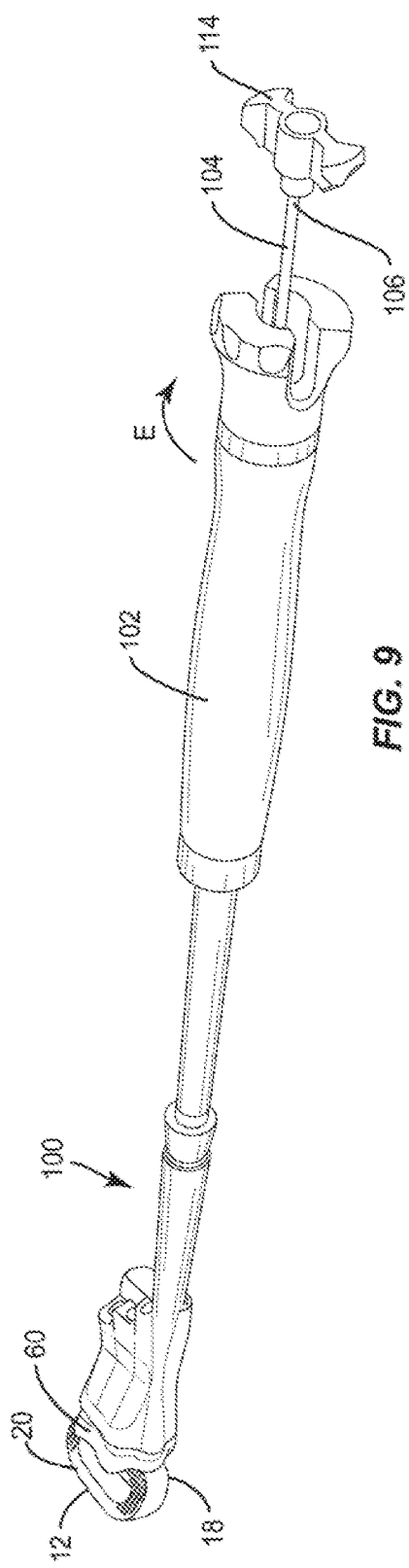
FIG. 9 is a perspective view of components of one embodiment of a system in accordance with the principles of the present disclosure.
Figure 10:
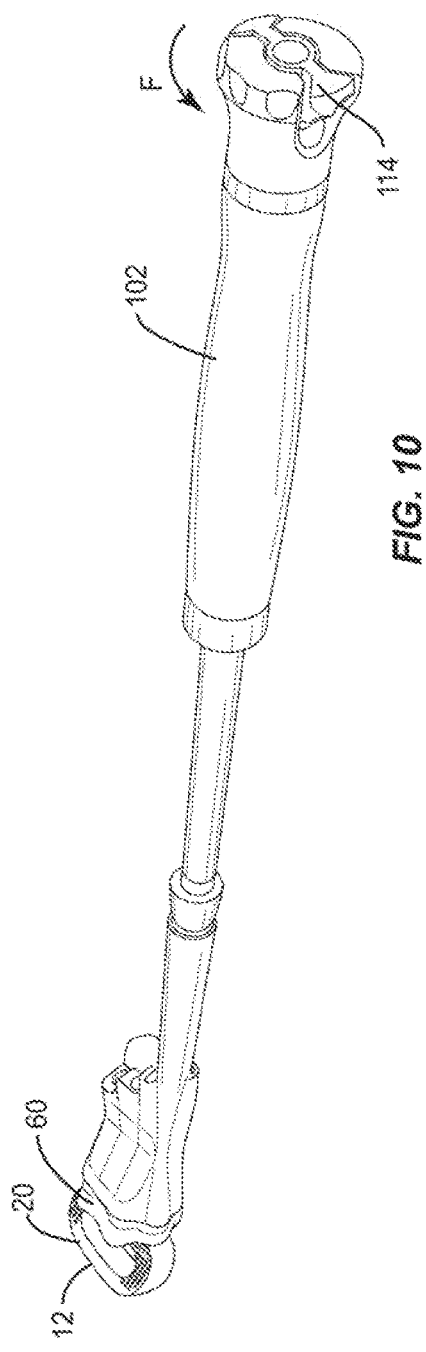
FIG. 10 is a perspective view of components of one embodiment of a system in accord with the principles of the present disclosure.

In one embodiment, as shown in FIGS. 7 and 8, spinal implant system 10, similar to the system described with regard to FIGS. 1-6, includes an ALIF plate 60 disposed with interbody implant 12, which are configured for implantation along surgical pathway PA. Plate 60 has a portion 62 configured to engage a vertebra V1 (FIGS. 13 and 14 in phantom) and a portion 64 configured to engage a vertebra V2 (FIGS. 13 and 14). Plate 60 includes an implant engaging surface 61 configured to engage surface 14 of interbody implant 12. In one embodiment, surface 61 is arcuate.

In some embodiments, surface 61 may have various configurations, such as, for example, planar, irregular, uniform, non-uniform, consistent, and variable. In some embodiments, surface 61 may be textured, rough, porous, semi-porous, dimpled and/or polished to facilitate or prevent movement and/or rotation relative to surface 14. In some embodiments, plate 60 may be attached with interbody implant 12 prior to implantation or in situ.

Plate 60 includes a flange 80 having an inner surface 82. Surface 82 defines a cavity, such as, for example, a passageway 84. Passageway 64 is disposed with interbody implant 12 for orientation with passageway 26 to implant a fastener in substantial parallel alignment with axis XB (FIG. 14) to attach plate 60 and interbody implant 12 with tissue, such as, for example, vertebrae V. Passageway 84 is disposed in a substantially perpendicular orientation relative to face A. Passageway 84 is oriented with the body of interbody implant 12 in substantial alignment with surgical pathway PA, as described herein. Plate 60 includes an inner surface 66 that defines openings 68 configured for disposal of bone fasteners, as described herein, to attach plate 60 and interbody implant 12 with tissue, such as, for example, vertebrae V. In one embodiment, plate 60 includes a back out element 70 engageable with the bone fasteners to resist and/or prevent disengagement and/or removal of the bone fasteners from tissue, such as, for example, vertebrae V and/or implant 12 and/or plate 60.

Spinal implant system 10 includes one or more fasteners, not shown, for attaching interbody implant 12 and/or plate 60 with tissue, as described herein. In some embodiments, the fasteners may be engaged with tissue in various orientations, such as, for example, series, parallel, offset, staggered and/or alternate vertebral levels. In some embodiments, one or more of the fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, dips, snaps, friction fittings, compressive fittings, expanding rivets, staples, nails, adhesives, posts, fixation plates and/or posts.

In one embodiment, as shown in FIGS. 9-12, spinal implant system 10, similar to the systems described with read to FIGS. 1-8, includes a surgical instrument, such as, for example, an ALIF modular drill, tap, and screw (DTS) guide 100. Guide 100 is connected with interbody implant 12, plate 60 and/or bone fasteners for orientation and delivery of the components of system 10 along surgical pathway PA, as described herein. Guide 100 introduces the components of spinal implant system 10 along surgical pathway PA to implant interbody implant 12, plate 60 and/or bone fasteners in substantial parallel alignment with axis XB (FIG. 14) to attach interbody implant 12, plate 60 and/or bone fasteners with tissue, such as, for example, vertebrae V.

Guide 100 mates with an inserter 102. Inserter 102 includes a removable shaft 104 that extends through inserter 102 and between a proximal end 106 and a distal end 108. End 108 includes a threaded portion 112 configured to engage pivot rod 40. End 106 includes an actuator 114 configured to manipulate engagement of threaded portion 112 with pivot rod 40. Shaft 104 is inserted through inserter 102, guide 100, plate 60 and into pivot rod 40 such that threaded portion 112 engages pivot rod 40.

Actuator 114 is rotated in a first direction to engage threaded portion 112 with a threaded portion of pivot rod 40. Engagement of shaft 104 with pivot rod 40 causes inserter 102 to become rigid to facilitate implantation. To allow for pivotal movement of plate 60 relative to interbody implant 12, actuator 114 is rotated in a second direction, opposite the first direction, causing threaded portion 112 to partially disengage from pivot rod 40 to facilitate relative freedom of movement such that the practitioner can maneuver the spinal implant for final placement of interbody implant 12 and/or plate 60. This configuration allows plate 60 to toggle relative to interbody implant 12, which provides interbody implant 12 and plate 60 relative freedom of movement such that the practitioner can maneuver the spinal construct for final placement of interbody implant 12 and/or plate 60. In some embodiments, plate 60 can rotate relative to interbody implant 12 about anterior face A of interbody implant 12 in a range of approximately 20 degrees, as shown in FIG. 12.

Inserter 102 is an adaptable instrument configured to perform multiple applications during a surgical procedure. In some embodiments, inserter 102 can prepare and/or create a cavity in tissue, such as, for example, bone. Inserter 102 guides a surgical instrument, such as, for example, a drill, tap and/or an awl, as well as guiding fasteners to penetrate tissue. In some embodiments, inserter 102 is a guide that holds plate 60 and interbody implant 12 together. Surgical instruments including an awl, a tap and screws are passed through inserter 102.

Figure 11:
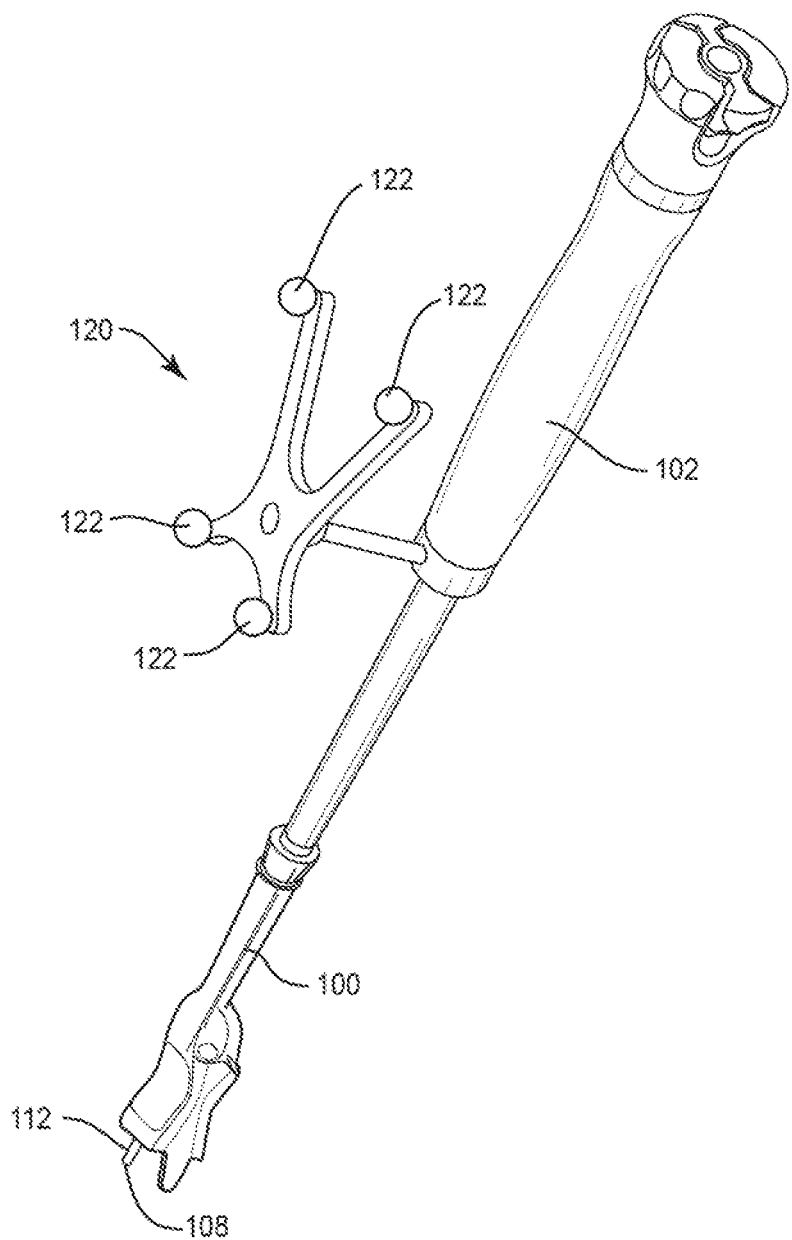
FIG. 11 is a perspective view of components of one embodiment of a system in accordance with the principles of the present disclosure.

In one embodiment, as shown in FIG. 11, inserter 102 includes image guidance and/or surgical navigation to monitor, maintain, adjust and/or confirm disposal, delivery and/or alignment of the components of system 10 along surgical pathway PA to implant interbody implant 12, plate 60 and/or bone fasteners in substantial alignment with axis XB to attach interbody implant 12, plate 60 and/or bone fasteners with tissue, such as, for example, vertebrae V. Inserter 102 includes surgical navigation components of system 10 to facilitate placement of interbody implant 12 with an intervertebral space.

The surgical navigation components of system 10 include an emitter 120 configured to generate a signal representative of a position of inserter 102 and/or interbody implant 12 connected therewith, for example, along surgical pathway PA and/or adjacent to a surgical site. In some embodiments, emitter 120 may include one or a plurality of emitters. In one embodiment, emitter 120 is shaped substantially like the Greek letter pi and comprises four spaced apart emitters 122, for generating a signal representing the trajectory of inserter 102 and/or interbody implant 12 relative to a portion of a patient's anatomy and the depth of inserter 102 and/or interbody implant 12 along surgical pathway PA and/or adjacent to a surgical site. In one embodiment, emitter 120 includes at least one light emitting diode. In some embodiments, emitter 120 may include other tracking devices capable of being tracked by a corresponding sensor array, such for example, a tracking device that actively generates acoustic signals, magnetic signals, electromagnetic signals, radiologic signals. In some embodiments, emitter 120 may be removably attached to inserter 102. In some embodiments, emitter 120 may be integrally formed with inserter 102 such that inserter 102 is a monolithic, unitary body.

In some embodiments, system 10 includes a tracking device (not shown) having an emitter array including one or a plurality of emitters that generate signals representing the position of various body reference points of the patient's anatomy. A sensor (not shown) receives signals from emitter 120 and the array. The sensor communicates with a processor (not shown), such as, for example, a digitizer control unit, which processes the signals from emitter 120 and the array to provide information regarding the trajectory of inserter 102 and/or interbody implant 12 relative to a portion of the patient's anatomy and the depth of inserter 102 and/or interbody implant 12 along surgical pathway PA and/or adjacent to a surgical site. The processor sends this information to a monitor, which provides a visual representation of the position of inserter 102 and/or interbody implant 12 along surgical pathway PA and/or adjacent to a surgical site to allow the medical practitioner to guile interbody implant 12 to a desired location within the patients anatomy.

The monitor is configured to generate an image from a data set stored in a controller, such as, for example, a computer. In some embodiments, the data set may be generated preoperatively using scanning techniques, such as, for example, a CAT scanner or MRI scanner. The image data set includes reference points for at least one body part, such as, for example, the spine of a patient, which has a fixed spatial relation to the body part. The processor is connected to the monitor, under control of the computer, and to inserter 102 and/or interbody implant 12.

The sensor receives and triangulates signals generated by emitter 120 and the array to identify the relative position of each of the reference points and inserter 102 and/or interbody implant 12 along surgical pathway PA to implant interbody implant 12, plate 60 and/or bone fasteners in substantial alignment with axis XB. The processor and the computer modify the image data set according to the identified relative position of each of the reference points during the procedure. The position and trajectory of inserter 102 and/or interbody implant 12 provided by emitter 120 and the array is processed by the processor and the computer and is visually displayed against the preoperative image data set stored in the computer to provide the medical practitioner with a visual representation of the trajectory of inserter 102 and/or interbody implant 12 relative to a portion of the patients anatomy and the depth of inserter 102 within the patient's anatomy. See, for example, similar surgical navigation components and their use as described in U.S. Pat. Nos. 6,021,343, 6,725,080, 6,796,988, the entire contents of each of these references being incorporated by reference herein In assembly, operation and use, as shown in FIGS. 13 and 14, spinal implant system 10, similar to the systems and methods described herein, is employed with an ALIF procedure in the lower lumbar region along surgical pathway PA to implant interbody plant 12, plate 60 and/or bone fasteners in substantial parallel alignment with axis XB to attach interbody implant 12, plate 60 and/or bone fasteners with tissue, such as, for example, vertebrae V, as shown in FIG. 13, for treatment of a spinal disorder, such as those described herein, affecting a section of a spine of a patient. Spinal implant system 10 may also be employed with other surgical procedures.

To treat the affected section of vertebrae V using an ALIF technique and surgical pathway PA, body B is disposed on its back, relative to a surgical fixed surface, such as, for example, a surgical table configured for supporting body B. An incision is made with a surgical instrument, such as, for example, a scalpel, for substantial alignment and communication to mate surgical pathway PA.

In some embodiments, a discectomy is performed adjacent the intervertebral space via surgical pathway PA. In some embodiments, sequential trial implants are delivered along surgical pathway PA and used to distract the intervertebral space and apply appropriate tension in the intervertebral space allowing for indirect decompression. In some embodiments, the size of interbody implant 12 is selected after trialing, interbody implant 12 is visualized by fluoroscopy and oriented before malleting into the intervertebral space.

Inserter 102 is connected with guide 100 to direct interbody implant 12 and/or plate 60 into body B along surgical pathway PA such that surface 20 is disposed in a cephalad orientation of body B and surface 18 is disposed in a caudal orientation of body B. Shaft 104 is inserted through inserter 102, guide 100, plate 60 and into pivot rod 40 such that threaded portion 112 engages pivot rod 40. Actuator 114 is rotated, in the direction shown by arrow E in FIG. 9, to engage threaded portion 112 with a portion of pivot rod 40. Engagement of threaded portion 112 with pivot rod 40 causes inserter 102 to become rigid and facilitates movement and/or implantation.

Inserter 102 delivers interbody implant 12 through the incision along surgical pathway PA adjacent to a surgical site for implantation into the intervertebral space. As shown in FIG. 14, anterior face A faces an anterior side of body B adjacent anterior portion A1 and posterior face P faces a posterior side P1 of body B, as described herein. Surface 20 engages endplate tissue of endplate E1 and surface 18 engages endplate tissue E2. To allow for pivotal movement of plate 80 relative to interbody implant 12, actuator 114 is rotated in the opposite direction, as shown by arrow F in FIG. 10, causing threaded portion 112 to partially disengage from pivot rod 40 to facilitate relative freedom of movement such that the practitioner can maneuver the spinal implant for final placement of interbody implant 12 and/or plate 60. As shown in FIG. 12, interbody implant 12 and/or plate 60 can be toggled in a first direction, as shown by arrow C, by approximately 10 degrees and in a second direction, as shown by arrow D, by approximately 10 degrees to properly fit and place interbody implant 12 and/or plate 60 in the intervertebral spam.

Pivot rod 40 is manipulated to align cavity 50 with passageway 26. Plate 60 is aligned with interbody implant 12 such that passageway 84 is aligned with passageway 26. Passageways 26, 84 and cavity 50 are aligned and oriented with interbody implant 12 in substantial alignment with surgical pathway PA, as described herein. A tap is disposed with guide 100 and pilot holes or the like are made in selected vertebra V1, V2 of vertebrae V, via surgical pathway PA. Passageways 26, 84 and cavity 50 are oriented to receive the fasteners via surgical pathway PA and disposed at an orientation such that the fasteners are delivered to the intervertebral space via surgical pathway PA and oriented to penetrate endplate tissue of an endplate. Passageways 26, 84 and cavity 50 guide bone fastener relative to axis XB and in substantial parallel alignment with surgical pathway PA. A driver (not shown) is disposed with guide 100 adjacent the intervertebral space and is manipulated to drive, torque, insert or otherwise connect bone fasteners with vertebrae V1, V2 adjacent the intervertebral space to attach interbody implant 12, plate 60 and/or bone fasteners with vertebrae V1, V2.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 15:
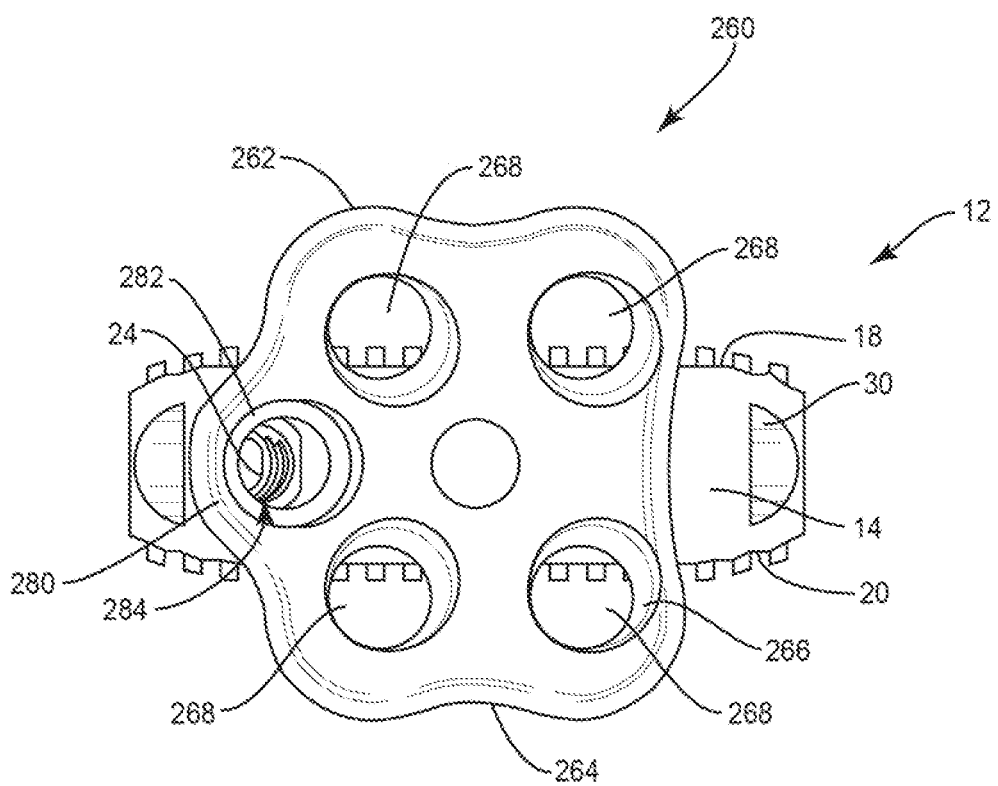
FIG. 15 is a side view of components of one embodiment of a system in accordance with the principles of the present disclosure.
Figure 18:
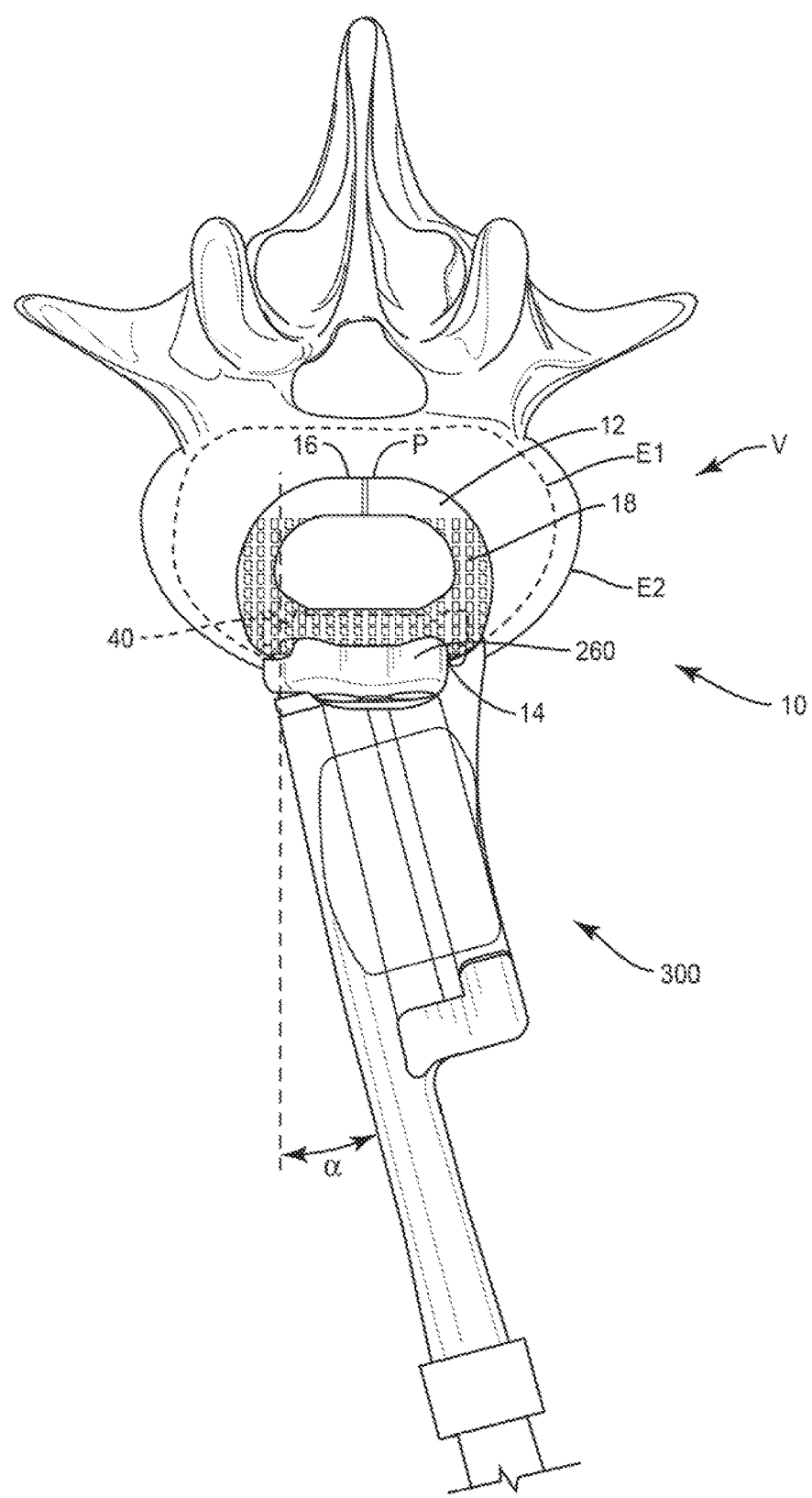
FIG. 18 is an axial view of components of one embodiment of a system in accordance with the principles of the present disclosure disposed with vertebrae.

In one embodiment, as shown in FIG. 15, spinal implant system 10, similar to the system described with regard to FIGS. 1-6, includes an OLIF plate 260 disposed with interbody implant 12, which are configured for implantation along surgical pathway PO, as described herein. Plate 260 has a portion 262 configured to engage a vertebra V1 (FIGS. 18 and 19 in phantom) and a portion 264 configured to engage a vertebra V2 (FIGS. 18 and 19). Plate 260 includes an implant engaging surface 261 configured to engage surface 14 of interbody implant 12. In one embodiment, surface 261 is arcuate.

Plate 260 includes a flange 280 having an inner surface 282. Surface 282 defines a cavity, such as, for example, a passageway 284. Passageway 284 is disposed with interbody implant 12 for orientation with passageway 24 to implant a fastener oblique relative to axis XB (FIG. 19) to attach plate 260 and interbody implant 12 with vertebrae V. Passageway 284 is disposed in a transverse orientation relative to face A. Passageway 284 is oriented with the body of interbody implant 12 in substantial alignment with surgical pathway PO, as described herein. Plate 260 includes an inner surface 266 that defines openings 268 configured for disposal of bone fasteners, as described herein, to attach plate 260 and interbody implant 12 with vertebrae V. Plate 260 includes a back out element 270 (FIG. 17) engageable with the bone fasteners to resist and/or prevent disengagement and/or removal of the bone fasteners from tissue, such as, for example, vertebrae V and/or implant 12 and/or plate 260. Spinal implant system 10 includes one or more fasteners, not shown, for attaching interbody implant 12 and/or plate 260 with tissue, as described herein.

Figure 16:
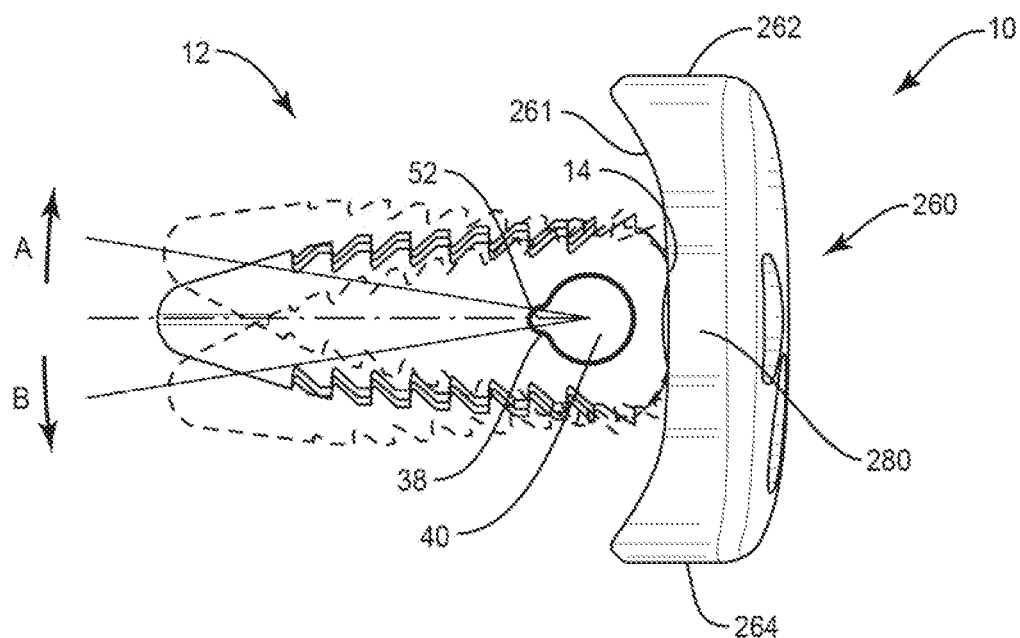
FIG. 16 is a side view of the components shown in FIG. 15.
Figure 17:
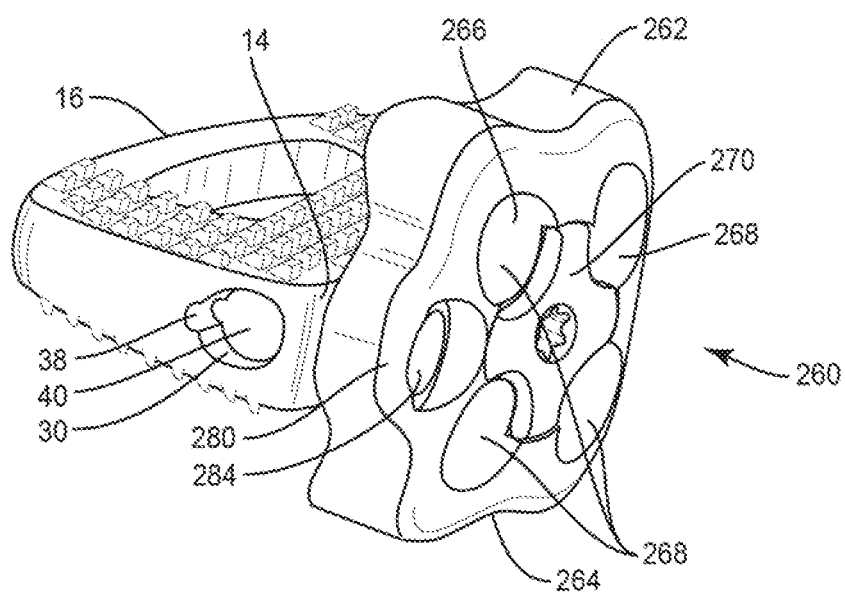
FIG. 17 is a perspective view of the components shown in FIG. 15.

In one embodiment, as shown in FIG. 18, spinal implant system 10, similar to the systems and methods described with regard to FIGS. 15-17, includes a surgical instrument, such as, for example, an OLIF modular drill, tap, and screw (DTS) guide 300, similar to guide 100 described herein. Guide 300 is connected with interbody implant 12, plate 260 and/or bone fasteners for orientation and delivery of the components of system 10 along surgical pathway PO, as described herein. Guide 300 introduces the components of system 10 along surgical pathway PO to implant interbody implant 12, plate 260 and/or bone fasteners oblique relative to axis XB to attach interbody implant 12, plate 260 and/or bone fasteners with vertebrae V.

In one embodiment, as shown in FIGS. 18 and 19, spinal implant system 10, similar to the systems and methods described herein, is employed with an OLIF procedure in a lower lumbar region between an L5 vertebral body and a sacrum S1 approach along surgical pathway PO to implant interbody implant 12, plate 260 and/or bone fasteners oblique relative to axis XB to attach interbody implant 12, plate 260 and/or bone fasteners with vertebrae V.

To treat the affected section of vertebrae V using the oblique surgical pathway PO, body B is disposed in a side orientation, relative to a surgical table. Body B is placed on a side, left side up. Body B is oriented such that the procedure can be performed obliquely in front of the iliac crest to provide direct access to the intervertebral space along surgical pathway PO, described herein, while avoiding selected muscular and abdominal anatomical structures. In some embodiments, placement of body B on its side facilitates access to surgical pathway PO that is disposed at oblique angle α relative to axis XB. An incision is made with a scalpel for substantial alignment and communication to create surgical pathway PO.

In some embodiments, a discectomy is performed adjacent the intervertebral space via surgical pathway PO. In some embodiments, sequential trial implants are delivered along surgical pathway PO and used to distract the intervertebral space and apply appropriate tension in the intervertebral space allowing for indirect decompression. In some embodiments, the size of interbody implant 12 is selected after trialing, interbody implant 12 is visualized by fluoroscopy and oriented before malleting into the intervertebral space.

An inserter (not shown), similar to inserter 102 described herein, is connected with guide 300 to direct interbody implant 12 and/or plate 260 and/or bone fasteners such that surface 18 is disposed in a cephalad orientation of body B and surface 20 is disposed caudal orientation of body B. A shaft disposed with the inserter is inserted through the inserter, guide 300, plate 260 and into pivot rod 40 such that the shaft engages pivot rod 40. The inserter delivers interbody implant 12 and/or plate 260 and/or bone fasteners through the incision along surgical pathway PO adjacent to a surgical site for implantation adjacent the intervertebral space.

Anterior face A faces an anterior side of body B adjacent anterior portion A1 and posterior face P faces a posterior portion P1 of body B, as described herein. Surface 18 engages endplate tissue of endplate E1 and surface 20 engages endplate tissue E2. Implant body 12 and/or plate 260 can be toggled with guide 300, similar to that described herein.

Pivot rod 40 is manipulated to align cavity 48 with passageway 24. Plate 260 is manipulated to align passageway 284 with passageway 24. Passageways 24, 284 and cavity 48 are aligned and oriented with interbody implant 12 in substantial alignment with surgical pathway PO, as described herein. A tap is disposed with guide 300 and pilot holes or the like are made in selected vertebra V1, V2 of vertebrae V, via surgical pathway PO, for receiving the fasteners. Passageways 24, 284 and cavity 48 are oriented to receive the fasteners via surgical pathway PO and is disposed at an orientation such that the fasteners are delivered to the intervertebral space via surgical pathway PO and oriented to penetrate endplate tissue of an endplate. Passageways 24, 284 and cavity 48 guide fasteners oblique relative to axis XB and in substantial alignment with surgical pathway PO, A driver (not shown) is disposed with guide 300 adjacent the intervertebral space and is manipulated to drive, torque, insert or otherwise connect bone fasteners with vertebrae V1, V2 adjacent the intervertebral space to attach interbody implant 12, plate 260 and/or bone fasteners with vertebrae V1, V2.

Upon completion of a procedure, similar to that described herein, the surgical instruments, assemblies and non-implanted components of spinal implant system 10 are removed and the incision(s) are closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
   a substantially cylindrical member; and
   an implant body extending between an anterior surface and a posterior surface, and including a first vertebral engaging surface and a second vertebral engaging surface,
   the implant body further including an inner surface that defines a portion of a first cavity and a portion of a second cavity spaced from the first cavity,
   the first cavity being oriented to implant a fastener oblique relative to a bilateral axis of a subject body and the second cavity being oriented to implant a fastener in substantial alignment with the bilateral axis,
   wherein the inner surface further defines a transverse bore, the member being disposed entirely within the transverse bore, and
   wherein the member includes a threaded surface defining a portion of the first cavity and a threaded surface defining a portion of the second cavity.

2. A spinal implant as recited in claim 1, wherein the first vertebral engaging surface and the second vertebral engaging surface are alternately disposable in a cephalad orientation of the subject body.

3. A spinal implant as recited in claim 1, wherein the first cavity is disposable in alignment with an oblique surgical pathway and the second cavity is disposable in alignment with an anterior surgical pathway.

4. A spinal implant as recited in claim 1, wherein the first cavity defines a longitudinal axis disposable at an angle relative to the bilateral axis, the angle being in a range of approximately 0-60 degrees.

5. A spinal implant as recited in claim 1, wherein the first cavity defines a longitudinal axis disposable at an angle of approximately 15 degrees relative to the bilateral axis and substantially aligned with an oblique surgical pathway such that the first cavity is configured to receive the fastener via the pathway.

6. A spinal implant as recited in claim 1, wherein the member is movable relative to the implant body along an axis defined by the transverse bore.

7. A spinal implant as recited in claim 1, wherein the member is rotatable relative to the implant body about an axis defined by the transverse bore when the member is disposed in the transverse bore.

8. A spinal implant as recited in claim 7, wherein the member is rotatable relative to the implant body in a range of rotation of approximately 20 degrees.

9. A spinal implant as recited in claim 7, wherein the member is rotatable relative to the implant body in a range of rotation of approximately 10 degrees in a first direction and approximately 10 degrees in a second direction.

10. A spinal implant as recited in claim 1, wherein the member is movable relative to the implant body and includes a stop configured to resist and/or prevent such movement.

11. A spinal implant as recited in claim 10, wherein the stop resists and/or prevents movement in a first direction and a second direction.

12. A spinal implant comprising:
    a substantially cylindrical member; and
    an implant body extending between an anterior surface and a posterior surface, and including a first vertebral engaging surface and a second vertebral engaging surface, wherein the first vertebral engaging surface and the second vertebral engaging surface are alternately disposable in a cephalad orientation of a subject body;
    the implant body further including an inner surface that defines a portion of a first cavity and a portion of a second cavity spaced from the first cavity, the implant body defining a transverse bore, the member being disposed entirely within the transverse bore such that the member is translatable and rotatable relative to the implant body when the member is disposed in the transverse bore,
    wherein the member includes a threaded surface defining a portion of the first cavity and a threaded surface defining a portion of the second cavity, and
    wherein the first cavity is configured to be oriented to implant a fastener oblique relative to a bilateral axis of the subject body and the second cavity is configured to be oriented to implant a fastener in substantial alignment with the bilateral axis, the first cavity defining a longitudinal axis disposed at an angle disposed in a range of approximately 0-60 degrees relative to the bilateral axis.

13. A spinal implant comprising:
    an implant body extending between an anterior surface and a posterior surface, and including a first vertebral engaging surface and a second vertebral engaging surface, the implant body further including a transverse bore, a first passageway and a second passageway that is spaced apart from the first passageway; and
    a substantially cylindrical member disposed entirely within the transverse bore such that the member is rotatable relative to the implant body when the member is disposed in the transverse bore, the member comprising a first cavity oriented to implant a first fastener through the first passageway and a second cavity oriented to implant a second fastener through the second passageway,
    wherein the member includes a threaded surface defining a portion of the first cavity and a threaded surface defining a portion of the second cavity.

14. A spinal implant as recited in claim 13, wherein the first cavity is configured to be oriented to implant the first fastener oblique relative to a bilateral axis of a subject body and the second cavity is configured to be oriented to implant the second fastener in substantial alignment with the bilateral axis.

15. A spinal implant as recited in claim 13, wherein the member is translatable relative to the implant body along an axis defined by the transverse bore.

16. A spinal implant as recited in claim 13, wherein the member is rotatable relative to the implant body in a range of rotation of approximately 10 degrees in a first direction and approximately 10 degrees in a second direction.

17. A spinal implant as recited in claim 13, wherein the member is movable relative to the implant body and includes a stop configured to resist and/or prevent such movement.

18. A spinal implant as recited in claim 17, wherein the stop resists and/or prevents movement in a first direction and a second direction.

19. A spinal implant as recited in claim 17, wherein a surface of the implant that defines the transverse bore includes a recess disposed along at least a portion of the transverse bore, the recess being engageable with the stop to limit a range of movement of the member.

20. A spinal implant as recited in claim 13, wherein the member is a pivot rod.

\* \* \* \* \*

UNITED STATES PATENT AND TRADEMARK OFFICE
CERTIFICATE OF CORRECTION

| | |
|---|---|
| PATENT NO. | : 10,188,525 B2 |
| APPLICATION NO. | : 15/094544 |
| DATED | : January 29, 2019 |
| INVENTOR(S) | : Carrie L. Gowan |

It is certified that error appears in the above-identified patent and that said Letters Patent is hereby corrected as shown below:

In the Specification

In Column 1, Line 4, delete "2014," and insert -- 2014, now Pat. No, 9,364,341, --, therefor.

In Column 1, Line 7, delete "HELD" and insert -- FIELD --, therefor.

Figure 5:
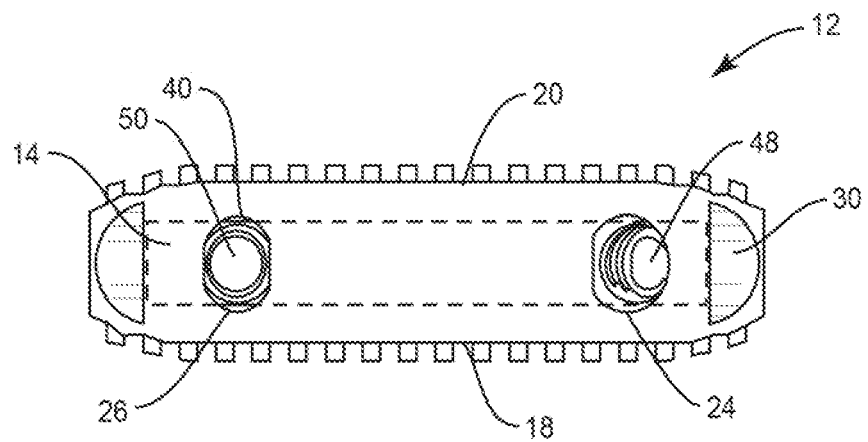
FIG. 5 a side view of the components shown in FIG. 1.
Figure 6:
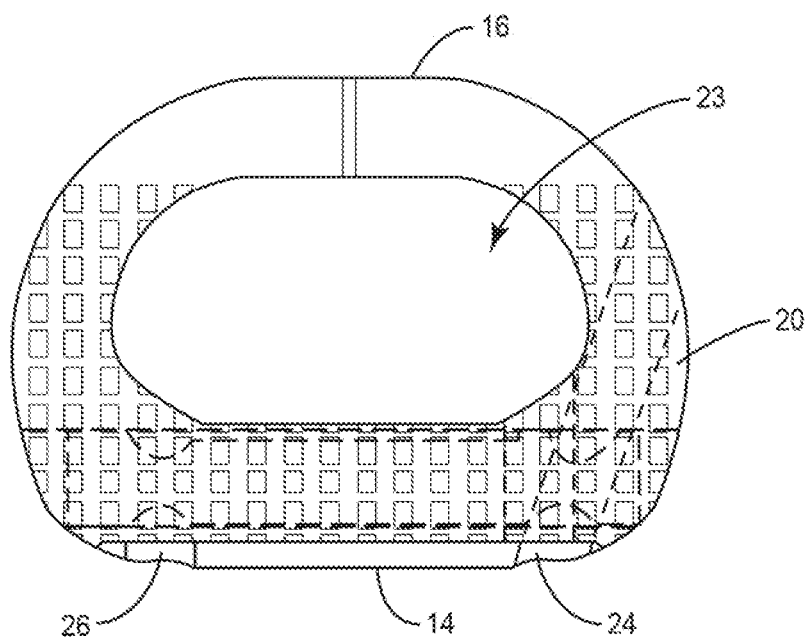
FIG. 6 is a side view of the components shown in FIG. 5.

In Column 1, Line 63, delete "FIG. 5 a" and insert -- FIG. 5 is a --, therefor.

In Column 2, Line 7, delete "accord with" and insert -- accordance with --, therefor.

In Column 2, Line 15, delete "FIG. 13 an" and insert -- FIG. 13 is an --, therefor.

In Column 3, Line 5, delete "an or" and insert -- an orientation --, therefor.

In Column 3, Line 7, delete "oft direct a" and insert -- off direct an --, therefor.

In Column 3, Line 16, delete "procedures-specific" and insert -- procedure-specific --, therefor.

In Column 3, Line 31, delete "ire one" and insert -- in one --, therefor.

In Column 4, Line 15, delete "embodiment, it" and insert -- embodiment. It --, therefor.

In Column 5, Lines 26-27, delete "trilcium phosphate," and insert -- tricalcium phosphate, --, therefor.

In Column 5, Line 52, delete "mated" and insert -- coated --, therefor.

In Column 6, Line 49, delete "and or" and insert -- and/or --, therefor.

In Column 7, Line 5, delete "OLIF approach." and insert -- ALIF approach. --, therefor.

Signed and Sealed this
Sixteenth Day of July, 2019

Andrei Iancu
*Director of the United States Patent and Trademark Office*

CERTIFICATE OF CORRECTION (continued)
U.S. Pat. No. 10,188,525 B2

In Column 7, Line 32, delete "body 6," and insert -- body B, --, therefor.

In Column 7, Line 49, delete "ax XB" and insert -- axis XB --, therefor.

In Column 7, Line 64, delete "a cavity" and insert -- a cavity, --, therefor.

In Column 7, Line 65, delete "shorn" and insert -- shown --, therefor.

In Column 8, Line 33, delete "Cavity 46" and insert -- Cavity 48 --, therefor.

In Column 8, Line 66, delete "snow" and insert -- arrow --, therefor.

In Column 9, Line 28, delete "Passageway 64" and insert -- Passageway 84 --, therefor.

In Column 9, Line 55, delete "dips," and insert -- clips, --, therefor.

In Column 9, Line 60, delete "read to" and insert -- regard to --, therefor.

In Column 11, Line 1, delete "such for" and insert -- such as, for --, therefor.

In Column 11, Line 23, delete "guile" and insert -- guide --, therefor.

In Column 11, Line 24, delete "patients" and insert -- patient's --, therefor.

In Column 11, Line 50, delete "patients" and insert -- patient's --, therefor.

In Column 11, Line 60, delete "plant 12," and insert -- implant 12, --, therefor In Column 12, Line 7, delete "to mate" and insert -- to create --, therefor.

In Column 12, Line 38, delete "plate 80" and insert -- plate 60 --, therefor.

In Column 12, Line 49, delete "spam." and insert -- space. --, therefor.

In Column 12, Line 63, delete "fastener relative" and insert -- fasteners relative --, therefor.

In Column 13, Line 30, delete "FIG. 15," and insert -- FIGS. 15-17, --, therefor.

In Column 14, Line 42, delete "disposed caudal" and insert -- disposed in a caudal --, therefor.

In Column 15, Line 5, delete "PO, A driver" and insert -- PO. A driver --, therefor.